(12) United States Patent
Johnson

(10) Patent No.: US 8,901,324 B2
(45) Date of Patent: Dec. 2, 2014

(54) TRIOXOLANE AND RELATED STABILIZED OXYGEN MOLECULES BASED TREATMENT PRODUCT

(71) Applicant: Benjamin Johnson, Evergreen, CO (US)

(72) Inventor: Benjamin Johnson, Evergreen, CO (US)

( * ) Notice: Subject to any disclaimer, the term of this patent is extended or adjusted under 35 U.S.C. 154(b) by 0 days.

(21) Appl. No.: 13/894,068

(22) Filed: May 14, 2013

(65) Prior Publication Data

US 2013/0303789 A1    Nov. 14, 2013

Related U.S. Application Data

(60) Provisional application No. 61/646,606, filed on May 14, 2012.

(51) Int. Cl.
| | |
|---|---|
| *A61K 8/49* | (2006.01) |
| *A61Q 19/08* | (2006.01) |
| *A61Q 19/00* | (2006.01) |
| *A61Q 19/02* | (2006.01) |
| *A61Q 11/00* | (2006.01) |

(52) U.S. Cl.
CPC ............. *A61K 8/4973* (2013.01); *A61Q 19/02* (2013.01); *A61Q 19/08* (2013.01); *A61Q 19/00* (2013.01); *A61Q 11/00* (2013.01)
USPC .......................................... 549/431

(58) Field of Classification Search
USPC .......................................... 549/431
See application file for complete search history.

(56) References Cited

U.S. PATENT DOCUMENTS 5,364,879 A * 11/1994 Herman .................. 514/452

* cited by examiner

*Primary Examiner* — Kristin Vajda
(74) *Attorney, Agent, or Firm* — Mark D. Trenner; Trenner Law Firm, LLC

(57) ABSTRACT

A treatment product including trioxolanes or related stabilized oxygen molecules. Just as oxidation is a somewhat violent electron transfer that results in amino acid malformation, only a molecule with similar electron attraction potential, another oxygen species in the form of a stabilized trioxolane or equivalent, can reverse such damage in most cases. The human body has the ability to fix such oxidation on its own, but this ability declines with age and excess damage. The treatment product described herein including trioxolanes, assists the body in this natural process. The result is reduction of inflammation, aging, and other conditions of the human body.

17 Claims, No Drawings

TRIOXOLANE AND RELATED STABILIZED OXYGEN MOLECULES BASED TREATMENT PRODUCT

CROSS REFERENCE TO RELATED APPLICATIONS

This application claims the priority benefit of U.S. Provisional Patent Application No. 61/646,606 filed May 14, 2012 for "Trioxolane and related stabilized oxygen molecules," incorporated by reference in its entirety as though fully set forth herein.

BACKGROUND

Trioxolane compounds are known in the pharmaceutical field for treating or preventing medical conditions. U.S. Pat. No. 5,364,879 for "Medical Uses Of Trioxolane And Diperoxide Compounds" of Herman discloses a trioxolane compound defined as a compound with the following structure where R and R' represent the same or different organic moieties. The carbons may also have additional organic moiety branches.

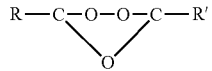

Herman discusses treating certain diseases, but several new potential uses for trioxolanes have been discovered including skin conditions such as age spots and melasma. Dermatologists typically distinguish skin conditions such as these from a "disease" such as melanoma or skin cancer. Therefore, Herman and others have not yet addressed the use of trioxolane for treating skin conditions and other medical concerns that result from protein oxidation because they were unaware of this alternative mechanism of action.

DETAILED DESCRIPTION

Treatment products and methods of treating a skin condition with trioxolane and related stabilized oxygen molecules are disclosed.

It has been postulated (and in many cases scientifically proven) that free radical damage is at the root of many diseases. The result is oxidation of proteins. Protein oxidation impacts cellular/tissue/organ health in a variety of ways. For example, protein oxidation can cause damage to hormones, peptides, proteins and cell walls directly resulting in cellular or immune system dysfunction. Protein oxidation can also cause reduced peptide, protein and hormone production, resulting from cellular/tissue/organ encumbrance due to a build-up of oxidized cellular components. Protein oxidation can also cause increased toxicity and immune dysfunction from the circulating oxidized proteins and peptides.

A treatment product is disclosed herein including trioxolanes and related stabilized oxygen species which have a novel mechanism of action including the ability to repair and remove oxidized proteins. This occurs as a result of the way in which the oxygen molecule is uniquely stabilized. Just as oxidation is a somewhat violent electron transfer that results in amino acid malformation, only a molecule with similar electron attraction potential, another oxygen species in the form of a stabilized trioxolane or equivalent, can reverse such damage in most cases.

The human body has the ability to fix such oxidation on its own, but this ability declines with age and excess damage. The treatment product described herein including trioxolanes, assists the body in this natural process. In addition, these very same stabilized oxygen species are needed to remove damaged proteins by dismantling them. Just as damaged proteins are a form of toxicity in the body, toxins inhaled or ingested can also be removed through the same dismantling process enhanced by the treatment product described herein. The net result of these combines benefits is the reduction of inflammation, aging and other conditions of the human body.

Before continuing, it is noted that as used herein, the terms "includes" and "including" mean, but is not limited to, "includes" or "including" and "includes at least" or "including at least."

In an example, a treatment product may be embodied as an internally administered supplement for the treatment of melasma. While melasma is considered a skin condition, it is postulated that it's origin is internal. It is noted that the term "skin condition" is defined herein according to well accepted definitions known in the dermatology arts, wherein melasma is not considered to be a disease, but rather a skin "condition."

Age spots are also considered a skin condition and not a disease. The mechanism of action of the treatment product is to repair protein oxidative damage to the dermal-epidermal junction, which reduces the signaling to the melanocyte that results in an age spot. Many treatments today reduce melanocyte production of melanin using tyrosinase inhibitors to lighten age spots, but the treatment product described herein goes to the source and heals the dermal-epidermal wound, thus preventing the age spot from forming in the first place. Accordingly the treatment product treats the origin of age spots.

Other skin conditions which may be treated include but are not limited to rosacea. Rosacea often involves internal digestive conditions which can be helped by the repair activity of trioxolane. Topically, trioxolane repairs oxidized proteins thereby reducing the burden on the immune system which allows the skin's associated redness to diminish.

Syringoma is another skin condition that can be treated as a result of trioxolanes ability to remove toxins and heal oxidative damage. We know that this condition shows up as swollen sebaceous glands on the face that are not responsive to any other therapy. Trioxolanes have the unique ability to remove the toxic presence and repair the damage at the gland thereby reversing the condition.

The treatment product may be administered sub-lingual. The treatment product may also be administered internally, for example, orally via a gel cap. Preferred dosing is at about 10% in a unique oil carrier that comprises almost all medium chain triglycrerides (MCT). This dramatically improves stability by reducing oxidation in the bottle which makes this form of trioxolane much more stable and potent. Topically, trioxolane reacts with water so a water-soluble form of the trioxolane (encapsulated in cyclodextrin) is made to enhance its efficacy.

The treatment product's unique ability to repair protein oxidation and remove toxins has been shown to be effective at treating Lyme Disease, Crohn's, diverticulitis, ulcerative colitis and interstitial cystitis.

It is noted that the treatment product includes the use of variations of trioxolanes. That is, there are mild adaptations to the molecule that may be used which do not substantially change its function for the purposes described herein, but technically change its Chemical Abstract Services CAS classification.

In an example where the skin condition is hyperpigmentation, a build-up of oxidized proteins in the skin results in the malfunction of melanocytes. The use of the treatment product including trioxolanes and/or related stabilized oxygen molecules, increases the dismantling of these oxidized proteins, in addition to increasing the repair of damaged proteins along the dermal-epidermal junction.

In an example where the skin condition is enlarged pores, an accumulation of oxidized proteins creates a sublayer of inflammation in the epidermis that pushes the skin upward, thereby expanding the opening of the follicle. The use of the treatment product including trioxolanes and/or related stabilized oxygen molecules, reduces this inflammation resulting in reduced size pores in the skin.

In an example where the skin condition is pen-oral dermatitis, acne and bug bites, the use of the treatment product including trioxolanes and/or related stabilized oxygen molecules, repair oxidized proteins that result from the inflammatory process while removing (e.g., with a dismantling process described below) toxins that may be the original source of inflammation.

The use of the treatment product including trioxolanes and/or related stabilized oxygen molecules may also be used for the treatment of melasma, or to slow and/or reverses aging effects in the body. The treatment product may also be used to oxidize toxins and thereby assisting in removal of toxins from the body (e.g., for treatment of allergies, reducing the side effects of chemotherapy and drug and/or alcohol ingestion), also repairing long term damage from the toxins. The treatment product may also be used to treat certain auto-immune diseases, organ dysfunction (kidney, liver, pancreas, thyroid, large and small bowel, stomach, spleen, adrenals, lungs), brain inflammation and related diseases (e.g., Parkinsons, Dementia and Alzheimers).

Another unique application is gum recession and tooth whitening. Both of these conditions are believed to be caused by a build-up of oxidized protein. In the case of yellow teeth, these oxidized proteins from food stick to the enamel. Weaker bonds can be brushed off but stronger bonds from certain foods/beverages may require a stronger extraction force. The stabilized oxygen in trioxolanes allows us to pull these oxidized particles from the teeth which whitens them dramatically. In the case of gum recession it is theorized that a build-up of oxidized proteins causes a retraction of the gum line. This product removes that build-up over time letting the gum return to its prior location which results in the first ever treatment for this condition.

An example formulation of a treatment product may include 10% trioxolane (or in the range of about 5-30% trioxolane), about 90% mct oil (or in the range of about 70-95% mct). Other components may also be included to supplement or enhance the effect(s) of the treatment product.

EXAMPLE

Product (10% trioxolane in MCT oil) was provided to 10 patients with yellow teeth. They were instructed to rinse it in their mouth and leave it in for at least 4 minutes before swallowing. Results after one month showed improvement in 9 out of 10 patients by an average of two shades.

EXAMPLE 2

Product (10% trioxolane in MCT oil) was provided to two patients with gum recession. After 60 days, both patients noted visible improvement that was estimated to be 20% better than the month prior.

EXAMPLE 3

Syringoma patient was provided both topical Product (10% trioxolane in cyclodextrin casing placed in a water-soluble formula) and oral product (10% trioxolane in MCT oil). She was instructed to put one pump topically and 10 drops sublingually twice daily. After two months she was 50% better. After 4 months she was 90% better.

EXAMPLE 4

10 cases of hyperpigmentation were treated with the topical preparation. One pump was applied to the age spots twice daily. 70% reported lightening within the first 30 days. Over 50% lightening was reported in 9 out of ten cases after 3 months of topical use.

EXAMPLE 5

5 cases of melasma were provided with the internal version of the product and told to use 10 drops twice daily. After three months, 4 people reported mild to dramatic lightening of their melasma. One case reported 95% resolution in just 60 days.

EXAMPLE 6

Lyme disease was tested using the internal Product. She took 10 drops twice daily for 9 months. All other therapies had failed and patient was on disability as a result of the severity of her condition. After three months patient was bloodwork negative for the spirochete but still symptomatic. After 9 months all of her symptoms had resolved and she was back to work.

EXAMPLE 7

5 patients were given the topical product for Rosacea. All 5 patients reported dramatic improvement in their condition within 2 weeks.

EXAMPLE 8

1 patient with interstitial cystitis reported dramatic improvement in her symptoms after two weeks on the internal product.

Many other case reports have been noted on a variety of benefits related to the internal and topical trioxolane products that can be provided at a future time.

It is noted that the examples shown and described are provided for purposes of illustration and are not intended to be limiting. Still other examples are also contemplated.

The invention claimed is:

1. A treatment product including about 1-50% trioxolanes in oil including at least medium-chain triglycerides (MCT).

2. The treatment product of claim 1, wherein the trioxolanes are selected to treat hyperpigmentation by application to an area of skin to be treated, wherein the trioxolanes increase dismantling of oxidized proteins resulting in the malfunction of melanocytes in the skin, and increase repair of damaged proteins along a dermal-epidermal junction of the skin.

3. The treatment product of claim 1, wherein the trioxolanes reduce a sublayer of inflammation in an epidermis of the skin, so that the sublayer does not push the skin upward, thus reducing openings of a follicle or pore size of the skin.

4. The treatment product of claim 1, wherein the trioxolanes are selected to treat peri-oral dermatitis, acne and bug bites, by application to an area of skin to be treated, to repair oxidized proteins that result from an inflammatory process while removing, through a dismantling process, toxins that are an original source of the inflammation.

5. The treatment product of claim 1, wherein the trioxolanes are selected to treat melasma, to slow and/or reverse skin aging effects related to oxidized protein build-up, autoimmune disease, organ dysfunction, brain inflammation, gum recession, and for tooth whitening.

6. The treatment product of claim 1, further comprising about 10% trioxolanes or related stabilized oxygen molecules.

7. The treatment product of claim 1, further comprising about 10% trioxolane.

8. An oral treatment product including about 1-50% trioxolane in oil including at least medium-chain triglyceride (MCT).

9. The oral treatment product of claim 8, further comprising about 10% trioxolane.

10. A topical treatment product including about 10% trioxolane in a cyclodextrin casing in a water-soluble formula.

11. The treatment product of claim 1, wherein the trioxolane is selected in an amount to promote teeth whitening.

12. The treatment product of claim 1, wherein the trioxolane is selected in an amount to treat Lyme disease.

13. The oral treatment product of claim 8, wherein the trioxolane is selected in an amount to promote teeth whitening.

14. The oral treatment product of claim 8, wherein the trioxolane is selected in an amount to treat Lyme disease.

15. The oral treatment product of claim 8, wherein the trioxolane is selected in an amount to heal melasma.

16. The oral treatment product of claim 8, wherein the trioxolane is selected in an amount to treat auto-immune disease.

17. The topical treatment product of claim 10, wherein the trioxolane is selected to treat peri-oral dermatitis, acne and bug bites, by application to an area of skin to be treated, to repair oxidized proteins that result from an inflammatory process while removing, through a dismantling process, toxins that are an original source of the inflammation.

* * * * *